United States Patent [19]

Hatfield, Jr. et al.

[11] Patent Number: 4,792,624

[45] Date of Patent: Dec. 20, 1988

[54] PROCESS FOR POLYMERIC MDA, RECYCLE OF FINISHED POLYMERIC MDA

[75] Inventors: Richard Hatfield, Jr., Pasadena; Howard R. Steele, Baytown; Nirad N. Shah, Houston, all of Tex.

[73] Assignee: The Dow Chemical Company, Midland, Mich.

[21] Appl. No.: 19,168

[22] Filed: Feb. 26, 1987

[51] Int. Cl.$^4$ ............................................. C07C 85/24
[52] U.S. Cl. ................................. 564/333; 564/331; 564/335
[58] Field of Search ............... 564/330, 331, 333, 335

[56] References Cited

U.S. PATENT DOCUMENTS

| | | | |
|---|---|---|---|
| 2,669,556 | 2/1954 | Sperati | 260/78 |
| 2,938,054 | 5/1960 | Demers et al. | 260/453 X |
| 2,974,168 | 5/1961 | Sharp et al. | 564/331 |
| 3,163,666 | 12/1964 | Kirss et al. | 260/453 OR |
| 3,260,751 | 7/1966 | Powers et al. | 564/331 |
| 3,274,247 | 9/1966 | Repper | 260/570 OR |
| 3,277,173 | 10/1966 | Powers et al. | 260/570 OR |
| 3,297,759 | 1/1967 | Curtiss et al. | 564/333 |
| 3,416,302 | 12/1968 | Knospe | 57/140 |
| 3,478,099 | 11/1969 | Ross et al. | 564/333 |
| 3,892,634 | 7/1975 | Hajek et al. | 564/331 X |
| 3,954,867 | 5/1976 | Funk et al. | 260/453 X |
| 4,083,870 | 4/1978 | Buysch et al. | 564/330 |
| 4,087,459 | 5/1978 | Knofel et al. | 564/331 |
| 4,089,901 | 5/1978 | Ziemek et al. | 564/330 |
| 4,093,658 | 6/1978 | Knofel et al. | 564/331 X |
| 4,094,907 | 6/1978 | Knofel et al. | 260/570 D |
| 4,147,224 | 4/1979 | Knofel et al. | 260/570 D |
| 4,189,354 | 2/1980 | Ellendt et al. | 260/453 X |
| 4,294,987 | 10/1981 | Prather et al. | 564/331 |

FOREIGN PATENT DOCUMENTS 1180795 2/1970 United Kingdom .
1569226 6/1980 United Kingdom .

Primary Examiner—Robert V. Hines
Attorney, Agent, or Firm—James S. Rose

[57] ABSTRACT

'An improvement is described in the process of preparing polymethylene polyphenyl polyamines by condensing aniline and formaldehyde in the presence of an acid catalyst. The improvement entails adding a minor proportion of a polyamine mixture comprising di(aminophenyl)methanes and oligomeric polymethylene polyphenyl polyamines, collectively known as polymethylene polyphenyl polyamines or polymeric MDA, to an intermediate stage of the condensation reaction where the various intermediately formed aminobenzylamines are present. The process lends itself to either a batch or continuous method for preparing the polyamines.

The improvement is actually observed in the polymethylene polyphenyl polyisocyanates derived from the polyamines which have substantially reduced color over those polyisocyanates prepared from polyamines prepared via a prior art method. Such color improvements invariably carry over to polyurethane products derived therefrom.

10 Claims, 1 Drawing Sheet

4,792,624

PROCESS FOR POLYMERIC MDA, RECYCLE OF FINISHED POLYMERIC MDA

BACKGROUND OF THE INVENTION

This invention relates to the preparation of polyamines and is more particularly concerned with an improved process for both batch and continuous preparation of methylene-bridged polyphenyl polyamines by acid condensation of aniline and formaldehyde.

DESCRIPTION OF THE PRIOR ART

The acid condensation of aniline and formaldehyde to produce a mixture of methylene-bridged polyphenyl polyamines containing a major portion of di(aminophenyl)methane is well-recognized in the art: see, for example, U.S. Pat. Nos. 2,938,054: 3,163,666; 3,260,751; 3,274,247; 3,277,173; 3,954,867; and 4,294,987. The mixture of polyamines can be used for a variety of purposes, for example, as a source of pure di(4-aminophenyl)methane (MDA) which is useful as an epoxy resin curative and an intermediate in the preparation of di(4-aminocyclohexyl)methane ($H_{12}$MDA). Both the MDA and $H_{12}$MDA are useful in the preparation of polyamides; see, for example, U.S. Pat. Nos. 2,669,556 and 3,416,302, respectively.

Alternatively, the mixture of polyamines can be phosgenated, by procedures well-known in the art to the corresponding mixture of polymethylene polyphenyl polyisocyanates containing methylenebis(phenyl isocyanate) as the major component. The latter can be recovered from said mixture, if desired, and finds broad application in the preparation of elastomeric and other noncellular polyurethanes. In addition, the mixture of polymethylene polyphenyl polyisocyanates obtained in the above phosgenation is widely used in industry in the manufacture of cellular polyurethanes.

The production of the polymethylene polyphenyl polyisocyanates and any inherent shortcomings are, for the most part, tied inextricably to the production of the precursor polyamines, collectively known as polymeric MDA. One of these shortcomings is the coloration of the polyisocyanate mixtures obtained. Highly colored polyisocyanates invariably lead to undesirable colorations in the polyurethane products derived therefrom and it is highly desirable to provide such polyisocyanates having reduced coloration.

Various distillation procedures and/or recycle steps have been employed in the art in search of a solution to this coloration problem and other undesirable components. For example, U.S. Pat. No. 4,189,354 describes additional distillation steps in purifying polymeric MDI mixtures and relates the product purification with reduced levels of hydrolyzable chlorine containing impurities. This is in turn related to improved color in the polyurethanes produced therefrom.

The art of recycling various components in the aniline/formaldehyde condensation has been widely tested. For example, U.S. Pat. No. 2,974,168 describes the recycling of oligomers having a higher boiling point than methylenedianiline back into the initial aniline/formaldehyde condensation step in order to increase overall methylenedianiline yield. U.S. Pat. Nos. 4,094,907 and 4,147,724 describe the recycling of unreacted aniline via a hydrophobic solvent back to a prior step in the aniline/formaldehyde condensation to avoid both amine distillation steps and formation of unwanted 2,2′-isomer formation.

British Pat. No. 1,180,795 discloses the recycling of 1 to 20 percent by weight of a polymethylene polyphenyl polyamine mixture back to the initial aniline/formaldehyde condensation in order to produce polyisocyanates having, what the reference refers to as, a useable viscosity. Additionally the reference discloses that the polyisooyanates so produoed react with organic compounds containing active hydrogens to give products having improved resistance to burning. British Pat. No. 1,569,226 discloses essentially the same aniline/formaldehyde condensation process as the previous British reference except that the portion of product recycled back to the aniline/formaldehyde condensation was in the acidified form. The purported advantages in this method are that serious plugging of the apparatus and excessive by-product formation was avoided.

There still remains a need to produce polymethylene polyphenyl polyisocyanates of reduoed color without resorting to distillation steps, discarding portions of the products containing high concentrations of hydrolyzable chlorine compounds, or introducing new solvent extraction procedures.

SUMMARY OF THE INVENTION

This invention is directed to an improved process for the preparation of a polyamine mixture comprising di(aminophenyl)methanes and oligomeric polymethylene polyphenyl polyamines by the acid catalyzed reaction of aniline with formaldehyde to sequentially form a mixture comprising aminobenzylamines which latter subsequently rearrange with heat to form a reaction product comprising said polyamine mixture, wherein the improvement comprises adding an aniline free mixture of di(aminophenyl)methanes and oligomeric polymethylene polyphenyl polyamines to said sequentially formed aminobenzylamines prior to their said rearrangement to said polyamine mixture.

This invention is also directed to a continuous process for the preparation of a polyamine mixture comprising di(aminophenyl)methanes and oligomeric polymethylene polyphenyl polyamines which process comprises the steps of:

(a) intimately intermixing at a temperature of about 0° C. to about 55° C., rapidly flowing streams of aqueous aniline hydrochloride and aqueous formaldehyde in the proportions of about 1.6 to about 8 moles of aniline per mole of formaldehyde, at the entry port of a continuous tubular reactor to form initially a mixture comprising aminobenzylamines;

(b) continuously passing said mixture from (a) through an intermediate cooling reaction zone wherein said aminobenzylamines can increase to at least about 30 percent by weight;

(c) continuously removing reaction mixture from said cooling zone at a rate corresponding to that at which reaction mixture is fed to said cooling zone;

(d) continuously passing said mixture from (c) through a rearrangement zone at a temperature of from about 60° C. to about 200° C. thereby forming said polyamine mixture;

(e) continuously removing said polyamine mixture from (d) at a rate corresponding to that at which the reaction mixture was fed into said rearrangement zone;

(f) continuously passing said mixture from (e) to a neutralizing zone oausing said hydrochloric acid component to be neutralized followed by distilling aniline and water from said polyamine mixture to produce an essentially aniline free polyamine mixture comprising said di(aminophenyl)methane and said oligomeric polymethylene polyphenyl polyamines;

(g) continuously removing said polyamine mixture from step (f) at a rate to correspond with that at which the reaction mixture was fed into said neutralizing and distilling zones;

(h) passing a major portion of said polyamine mixture product to storage while recycling a minor proportion to a subsequent step (b) described above in such proportions that said recycle polyamine comprises from about 1 to about 40 percent by weight based on the combined initial weights of aniline, aniline hydrochloride and formaldehyde; and (i) repeating steps (a) to (h) so as to continually pass said major proportion of polyamine mixture to storage while recycling the minor proportion back to step (b).

The terms "polyamine mixture comprising di(aminophenyl)methane and oligomeric polymethylene polyphenyl polyamines," "polymethylene polyphenyl polyamines," and "polymeric MDA" are all used interchangeably throughout the specification and claims. These terms include all the isomer distribution and oligomeric distributions known in the art.

Surprisingly, by the simple adjustments made in prior art processes as defined above, the polyamine mixtures produced in accordance with the present invention produce the corresponding polyisocyanate mixtures having greatly reduced color in comparison with prior art polyisocyanates similarly prepared but lacking the novel step herein described.

DETAILED DESCRIPTION OF THE INVENTION

Figure 1:
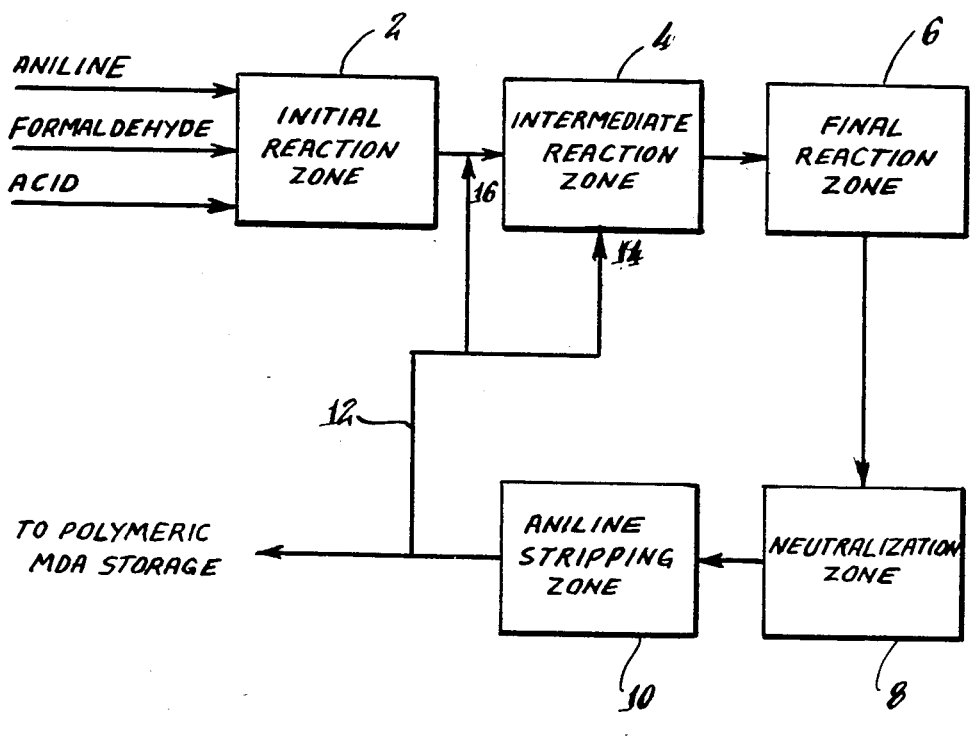
FIG. 1 shows a flow sheet illustrating in schematic form the process according to the invention.

The reaction between aniline and formaldehyde in the presence of a mineral acid such as hydrochloric acid has been the subject of considerable study over a prolonged period. It is generally recognized that the reaction occurs in stages—the last of which is generally conducted at relatively higher temperatures than the first. The various stages in the reaction so far as it relates to the preparation of the major product, namely di(aminophenyl)methane, can be represented schematically (see FORMULA CHART below).

The aniline and formaldehyde react to form, as a highly transient intermediate, methylene dianiline (I). It is believed that the symmetrical N,N',N''-triphenylhexahydrotriazine (II) is also formed at this stage and that its subsequent behaviour parallels the behavior of (I). The transient intermediates (I) and (II) then rearrange to form N-phenylaminobenzylamines. At least two such monomeric products are possible, namely, the p-isomer represented by the formula (III) and the corresponding o-isomer represented by the formula (IV). The principal isomer formed is normally the p-isomer (III) with the o-isomer as the minor component. As will be readily appreciated by one skilled in the art, the formation of the monomeric products (III) and (IV) is accompanied by formation of corresponding oligomeric products which can be represented by the generic formula (VII) wherein the free amino group is o- or p- with respect to the —$CH_2$—NH—bridging group, the multiple —CH—NH— groups are o- or p- with respect to their immediate neighbors and n is a whole number. The mixture of isomers (III) and (IV), and the oligomeric forms thereof, is hereinafter referred to as the "aminobenzylamines".

In the final sequence of the reaction, the aminobenzylamines (III) and (IV) rearrange to form the corresponding di(aminophenyl)methanes including the p,p'-isomer (V) and the o,p'-isomer (VI). It will be seen that rearrangement of (IV) can also give rise to the o,o'-isomer of di(aminophenyl)methane although, in the interests of simplicity, this particular isomer is not shown in the reaction scheme since it is generally not formed in any substantial amounts. It will be appreciated by one skilled in the art that the oligomeric forms (VII) of the aminobenzylamines will rearrange to give polymethylene polyphenyl polyamines but the formation of such products has not been shown in the reaction scheme in the interests of simplicity.

Of the various stages shown in the reaction scheme, the first two, namely the formation of the transient intermediates (I) and (II) and their rearrangement to the corresponding aminobenzylamines (III) and (IV), generally occur when the aniline and formaldehyde are brought together in the presence of mineral acid at ambient temperatures, i.e., of the order of about 25° C. without the application of external heat. The reaction is exothermic and, unless controlled by cooling, the temperature of the reaction mixture will rise substantially.

The final stage of the process, i.e., the rearrangement of the aminobenzylamines, will not take place at any significant rate until the reaction mixture is heated, generally to a temperature in excess of about 60° C. It will be readily understood that at any time in such a sequential process complex mixtures are present. Before the final stage but after the initial mixing of the reactants, the reaction mixture will contain inter alia, the aminals, the aminobenzylamines, and some already rearranged product.

The present process employs the above reactions but includes the novel step of adding a minor proportion of an aniline free mixture of di(aminophenyl)methanes and oligomeric polymethylene polyphenyl polyamines at that stage where the aminobenzylamines have been formed in at least about 10 percent, preferably at least 30 percent, most preferably at least 40 percent by weight based on the combined weights of said aminals, aminobenzylamines, and rearranged polyamines. It will be readily understood by one skilled in the art that the additive aniline free mixture of di(aminophenyl)methanes and oligomeric polymethylene polyphenyl polyamines and the polyamine mixture prepared by the process can be, and, preferably are, one and the same but are not so limited. Conversely, an aniline free mixture having entirely different proportions of components than those of the polyamine prepared in the process can be employed as an additive reagent. Additionally, additive polyamine mixtures having widely varying and differing 4,4-, 2,4'- and 2,2'-MDA isomer contents over the product polyamine are within the scope of the present invention. However, the preferable embodiment of using the same di(aminophenyl)methanes and oligomeric polymethylene polyphenyl polyamines produced in the process as the additive component in subsequent runs allows the present process to be readily adapted to a continuous one.

It is important to remove the aniline from the polyamine mixture before it is added to the aminobenzylamines in order to achieve maximum color improvement in the polyisocyanate. At the same time, the polyamine additive must be added at that point in the reaction sequence where aminobenzylamines are present and not at the site where the aniline and formaldehyde are first reacting. This also to achieve the improved color of the resulting polyisocyanates. The present point of addition of the polyamine in the sequence clearly distinguishes the present process over any of the prior art methods.

In the practice of the present process any of the prior art methods disclosed for condensing aniline with formaldehyde in the presenoe of an acid can be employed so long as the above novel step is included. For typical procedure for such condensations see U.S. Pat. Nos. 3,954,867 and 4,294,987 cited supra whose disclosures are incorporated herein by reference.

In order to facilitate further an understanding of the key step of the present process, reference is made to FIG. 1 which shows one embodiment of a continuous preparation of polymeric MDA. The initial reactants, aniline, strong acid catalyst either separate or premixed with the aniline, and formaldehyde are brought together rapidly in an INITIAL REACTION ZONE (2). This zone (2) can be any reaction vessel, series of piping, tubular reactor or the like as described in U.S. Pat. No. 3,954,867 already incorporated herein. It is in this zone where the transient aminals are immediately and exothermically formed and then just as immediately begin their transformation to the aminobenzylamines. The INTERMEDIATE REACTION ZONE (4) represents a cooled zone comprising a separate tank, vessel, piping or the like to which the mixture from (2) is conveyed. The conversion of aminals to aminobenzylamines in this zone is maximized along with some final unavoidable rearrangement of aminobenzylamines to polymeric MDA product. It is at this stage of the reaction sequence that the minor proportion of the aniline free mixture of di(aminophenyl)methanes and oligomeric polymethylene polyphenyl polyamines is added as noted by the transfer line (12) leading directly into the ZONE at (14). Alternatively, the amine mixture can be introduced at (16) prior to any specific tank or vessel to a site where the aminobenzylamines have not been completely maximized. In its broadest scope the INTERMEDIATE REACTION ZONE (4) includes the piping which conveys reaction mixture from (2) to (4). After the INTERMEDIATE ZONE (4) the sequence of steps are the known prior art methods for converting the aminobenzylamines to the polyamine mixture of di(aminophenyl)methanes and oligomeric polymethylene polyphenyl polyamines by heating in a FINAL REACTION ZONE (6), the neutralization of the acid polyamine in NEUTRALIZATION ZONE (8) followed by removing the unreacted aniline and water in the ANILINE STRIPPING ZONE (10) to obtain the product. Line (12) shows the transfer line for the polyamine back to the INTERMEDIATE REACTION ZONE (4) either at (14) or (16). In the event that a batch process was being employed, the ZONES (2), (4), and (6) would simply be the same reaction site, vessel, tank, or the like.

The formation of the intermediate aminobenzylamines is carried out in accordance with any of the procedures hitherto employed to achieve this first stage in the presence of a strong acid catalyst such as hydrochloric, hydrobromic, phosphoric, p-toluenesulfonic, methanesulfonic acids, and the like. A particularly preferred strong acid catalyst is hydrochloric acid. Advantageously, the aniline and formaldehyde are brought together under aqueous conditions in the presence of the strong acid and using appropriate agitation means or liquid injection means. The order in which the reactants are brought together is not critical.

The reaction between aniline and formaldehyde in the INITIAL REACTION ZONE (2) is exothermic but can be controlled satisfactorily either by appropriate adjustment of the rate of addition of reactants or by applying external cooling or by a combination of both techniques. Obviously, in a bathh or non-continuous process the exotherms can be easily controlled by the slow addition of formaldehyde to the mixture of aniline and acid. Although the reaction temperature in this stage of the reaction is not critical, it should not be lower than about 0° C. and it is preferable that the temperature in question does not rise above about 55° C. Preferably the reaction temperature at this stage of the reaction is maintained within the range of about 15° C. to 35° C.

The reaction between the aniline and formaldehyde to yield the intermediate aminobenzylamines in this first stage occurs very rapidly. The progress of the reaction can be followed by conventional analytical techniques, e.g. by following the disappearance of formaldehyde from the reaction mixture; by proton nuclear magnetic resonance analysis to determine the aminal; aminobenzylamine polyamine content of the mixture; by gel permeation chromatography or gas phase chromatography and the like.

The proportions in which the aniline, formaldehyde and acid catalyst are brought together in the above first stage of the process of the invention are determinative of the overall yield of diamine in the final polyamine mixture and, to a certain extent, of the proportion of o,p'-isomer to p,p'-isomer in the diamine component of said final mixture. Advantageously, the proportion of aniline to formaldehyde is at least 1.6 moles of the former for each mole of the latter. While the lower limit of aniline concentration is critical in terms of the overall result achieved in the process, the upper limit is free from such criticality and is dictated largely by economic considerations. An upper limit of about 8 moles of aniline per mole of formaldehyde conforms to the latter considerations. Generally, the proportion of aniline employed in the first stage of the process of the invention is within the range of about 2 to about 2.8 moles per mole of formaldehyde but proportions higher or lower than this can be employed if desired.

The amount of strong acid catalyst employed in the first stage of the process of the invention is advantageously in the range of about 0.1 mole to about 1 mole per mole of aniline and is preferably within the range of about 0.25 mole to about 0.8 mole per mole of aniline.

Advantageously, muriatic acid (30 to 37 percent aqueous hydrochloric acid) and about 37 percent by weight aqueous formalin solution are employed. Generally speaking, the overall water content in the reaction mixture will range from about 4 to 7 moles per mole of aniline or from about 7 to about 15 moles of water per mole of formaldehyde.

As it applies to a oontinuous process, the residence time for this initial step is not more than 120 seconds and preferably less than 20 seconds. However, in the case of a batch process the residence time will be controlled by the time for addition of the formaldehyde. This addition can be as short as the above period but preferably is from about 5 minutes to about 60 minutes.

Any time or reaction site after this period can be considered the INTERMEDIATE REACTION ZONE (4). The onset of the major exothermic phase of the reaction begins and the temperature is kept at or below about 60° C., preferably below about 50° C. in this ZONE. Advantageously, the time of cooling falls within a range of about 4 minutes to 90 minutes, preferably about 10 to about 60 minutes. The intermediate product mix at equilibrium will comprise, besides the excess aniline, acid, and water, a minor proportion of aminal, a considerable proportion of aminobenzylamines including oligomeric aminobenzylamines, and a considerable proportion of the desired polymeric MDA. Typically, the combined weight percents (based on 100 total) of aminals:aminobenzylamines:polymeric MDA can be (1 to 15):(10 to 70):(10 to 70).

The addition of the aniline free polyamine mixture of di(aminophenyl)methanes and oligomeric polymethylene polyphenyl polyamines can be effected anywhere to this intermediate zone provided the minimum proportions of aminobenzylamines have formed. The exact point of addition is not critical and can be a specific holding tank, agitated vessel, cooling loop of a reactor, conveyance piping, and the like, so long as it is not at the initial site of the aniline/formaldehyde condensation. The rate of addition is in no way critical but can be effected all at once or incrementally by batch or as continuous stream in a continuous process.

Regardless of its source, the polyamine mixture can be any of those polymeric MDA mixtures known in the art provided it be aniline free. Accordingly, polyamine mixtures which can be used are those wherein the di(aminophenyl)methane content is from about 20 to about 85 percent by weight (preferably about 35 to about 65 percent) with the remainder of the mixture being from about 80 to about 15 percent by weight (preferably about 65 to about 35 percent) of the polymethylene polyphenyl polyamines having a functionality greater than 2 or otherwise oligomeric polyamines. The isomer content is not critical and includes those wherein the 4,4'-isomer content falls within the range of 50 to 98 percent with 2,4'-content being 2 to 50 percent and the presence of very small proportions (i.e. less than 3 percent 2,2'-isomer).

Advantageously, the proportion in which the polyamine mixture is added falls within the range of about 1 to about 40 percent by weight based on the combined initial weight of the aniline, aniline salt formed from the acid catalyst and the equivalent amount of aniline, and formaldehyde, preferably it is from about 5 to about 25 percent.

It will be readily appreciated by one skilled in the art that in a continuous process in accordance with the present invention, the addition of the extra amine components in the polyamine mixture will have an effect on the overall reaction stoichiometry, and will even affect the viscosity of the polymeric MDA produced. Generally speaking, the viscosity increases. Accordingly, in an alternative, and, preferred, embodiment, the original aniline to formaldehyde ratio after the initial reaction is increased in subsequent steps by about 10 to about 50 percent provided the ratio still falls within the ranges set forth above. This results in lowering the polymeric MDA viscosity back to original levels.

Generally speaking, it is desirable to maintain a constant acid to aniline ratio, and, accordingly the ratio of acid is increased to accommodate the increased aniline levels set forth above and restore the originally chosen ratio.

At the next stage of reaction or FINAL REACTION ZONE (6) the mixture of aminobenzylamines polymeric MDA, and whatever minor amount of aminals is present is fully reacted or rearranged to the polymeric MDA product by subjecting the mixture to a temperature of from about 60° C. to about 200° C., preferably from about 80° C. to about 135° C. This can be carried out in a stirred reactor, either the same reaction kettle in which the initial condensation and intermediate reactions were performed, or, in the optional continuous method, in a reaction zone different from the other sites. The time to which the reaction mixture is subjected to the elevated temperatures will be sufficient to ensure completion of the formation of the methylene-bridged polyphenyl polyamines. The higher the temperature the shorter the period. The actual time required for completion for any given temperature can be determined readily by trial and error. Generally speaking, the residence time is within the range of about 60 minutes to about 400 minutes, preferably from about 100 to 240 minutes.

The reaction mixture is withdrawn from the final reaction step and the polymeric MDA recovered by procedures routine in the art. Whether by batch or continuous process, the recovery starts typically with neutralization of the reaction mixture with sodium hydroxide solution followed by separation of the organic phase in the so-called NEUTRALIZATION ZONE (8) with optional water washing to remove residual salt. This is followed by stripping of excess aniline and water in the ANILINE STRIPPING ZONE (10) using typically a conventional evaporator-stripper apparatus to provide the aniline free polyamine mixture of diaminophenyl(methanes) and oligomeric polymethylene polyphenyl polyamines.

At this stage, 100 percent of the product can be passed to storage. Alternatively, in the continuous process a major proportion can be passed to storage, while a minor proportion is recycled back via line (12) as the polyamine additive to the aminobenzylamine stage described above.

A most preferred continuous embodiment using aqueous hydrochloric acid in accordance with the present invention has been set forth above.

The mixture of methylene-bridged polyphenyl polyamines so obtained can be used in any one of a number of ways. For example, the mixture can be subjected to procedures such as fractional crystallization and fractional distillation under reduced pressure to separate the diamine content from the higher oligomers. The isolated diamine can be purified, if desired, using fractional crystallization or like techniques to obtain a product which is substantially pure 4,4'-isomer. The isolated diamine after purification, if desired, can then be used as such as a curative for epoxy resins or as an intermediate in the formation, by catalytic hydrogenation, of di(aminocyclohexyl)methane, which latter is itself useful as an intermediate, using methods well-known in the art, in the formation of polyamides, polyimides, and copolymers thereof. The isolated diamine can also be phosgenated to form the corresponding diisocyanate which finds wide application in the preparation of polyurethane and like polymers.

The oligomeric polyamines which remain after separation of the diamine in the above manner are also useful as curatives for epoxy resins and as intermediates in the preparation, by phosgenation, of the corresponding polymethylene polyphenyl polyisocyanates. The latter are widely known and used in the preparation of rigid polyurethane and polyisocyanurate foams and as adhesives and the like.

Alternatively, the mixture of diamine and oligomeric polyamines obtained in the process of the invention can be subjected, without separation of the individual components, to phosgenation to produce the corresponding mixture of methylenebis(phenyl isocyanates) and oligomeric polymethylene polyphenyl polyisocyanates. This mixture of isocyanates can be employed as such in the preparation of polyurethanes, polyisocyanurates and the like cellular and non-cellular polymers. On the other hand, the mixture of isocyanates can be separated into methylenebis(phenyl isocyanate) and a residue of the oligomeric polymethylene polyphenyl polyisocyanates using procedures such as those described in U.S. Pat. Nos. 3,471,543 and 3,892,634.

It is in the above phosgenation products that the unexpected benefits are observed for the products obtained by the present process. The polyisocyanates are characterized by greatly improved color over those polyisocyanates obtained form polyamine mixtures prepared by the prior art method which lacked the novel polyamine addition step.

The following examples describe the manner and process of making and using the invention and set forth the best mode oontemplated by the inventors of carrying out the invention but are not to be construed as limiting.

EXAMPLE 1

A one liter 4-neck Morton reaction flask is equipped with a mechanical stirrer, thermometer, temperature controller, nitrogen purge tube, condenser, and heating mantle. The flask is charged with 241.2 g. (2.6 moles) of aniline and 62.8 g. (0.63 mole) of 37 percent aqueous hydrochloric acid. While maintaining the temperature below about 50° C., 116.02 g. (1.43 moles) of 37 percent aqueous formalin is added with stirring over a period of 8 to 10 minutes. Following this, a 92.4 g. portion of a mixture comprising about 50 percent of di(aminophenyl)methane and the balance a mixture of oligomeric polymethylene polyphenyl polyamines is added to the reaction flask. This proportion of additive represents about 30 percent by weight of the original aniline, aniline hydrochloride and formaldehyde. This added polyamine mixture was previously prepared from another condensation of aniline with formaldehyde using the same conditions, proportions and ingredients set forth above. In this prior condensation, after the formalin addition the reaction mixture was held at 60° C. for 30 minutes followed by 95° C. for 4.0 hours. The resultant reaction product was neutralized using 50 percent aqueous caustic, washed with water, followed by distillation of the organic layer at 1 mm. Hg., 150° C. for 30 minutes to remove the unreacted aniline and to provide the polyamine additive.

The reaction mixture containing the additive polyamine is held at 60° C. for 30 minutes then heated at 95° C. with stirring for four hours.

The reaction mixture is neutralized using 50 percent aqueous caustic, washed with water followed by distillation of the organic layer at 1 mm. Hg., 150° C. for 30 minutes to remove the unreacted aniline and to provide a polyamine mixture (A) in accordance with the present process comprising di(aminophenyl)methane and oligomeric polymethylene polyphenyl polyamines.

A second polyamine mixture (B) in accordance with the present invention is prepared similarly to (A) above except that the proportion of polyamine recycled amounted to 25 percent of the aniline, aniline hydrochloride and formalin charge and the rearrangement temperature of 95° C. is maintained for only 2.5 hours. The two polyamine mixtures are characterized as follows:

|  | A | B |
|---|---|---|
| Viscosity (ctsk) at 90° C. | 635 | 635 |
| Isomer Distribution (%) |  |  |
| Di(aminophenyl)methane (MDA) |  |  |
| o,o' | 0.2 | 0.1 |
| o,p' | 5.6 | 5.0 |
| p,p' | 94.2 | 94.9 |
| Oligomeric Distribution (%)[1] |  |  |
| MDA | 44.2 | 43.4 |
| Trimer | 24.8 | 23.7 |
| Tetramer | 13.6 | 13.6 |
| Pentamer | 7.7 | 7.9 |
| Hexamer | 4.4 | 4.8 |
| Heptamer and higher oligomers | 5.4 | 6.6 |
| MMM %[2] | 0.2 | 0.6 |

[1] Oligomeric distribution determined by gel permeation chromatography.
[2] MMM represents monomethyl MDA weight percent based on the total MDA plus MMM present.

EXAMPLE 2

A continuous control process in accordance with the prior art for the production of a polyamine mixture of polymethylene polyphenyl polamines containing approximately 50 percent by weight of di(aminophenyl)methanes is carried out as follows.

The apparatus comprises a mixer nozzle through which a mixture of aqueous aniline hydrochloride solution and formalin solution (37% aqueous formaldehyde solution) is mixed in the proportions by weight such that the molar ratio of hydrochloric acid to aniline is 0.25 and the molar ratio of aniline to formaldehyde is 2.04. The reaction mixture is led through a reactor at 50° C. The apparatus up to this point and including the mixer nozzle represents the INITIAL REACTION ZONE. The reaction mixture is pumped to an intermediate reaction tank (INTERMEDIATE REACTION ZONE) which is held at 60° C. and wherein the residence time is about 22 minutes. The product from the intermediate reactor is pumped to a FINAL REACTION ZONE comprising a reactor at 93° C. with a residence time of about 62 minutes and through a reactor at 121° C. where the outlet is pumped to a NEUTRALIZATION ZONE.

Proton nuclear magnetic resonance analysis of a sample from the loop of the intermediate reaction tank analyzes out in percent by weight of aminals (formulae I and II above): aminobenzylamines (formulae II and IV): polymeric MDA as 11.0:58.6:30.4.

The acid polymeric MDA mixture is cooled to room temperature, neutralized by the addition of aqueous sodium hydroxide solution in the NEUTRALIZATION ZONE and the amine layer continually separated. The aniline is separated from the neutralized amine layer by distillation under reduced pressure in the ANILINE STRIPPING ZONE and recovered for recycle back to the original aniline charge. The residue is the polyamine mixture comprising di(aminophenyl)methane and oligomeric polymethylene polyphenyl polyamines. This polyamine mixture is continuously converted to the corresponding di(isocyanatophenyl)methane and oligomeric polymethylene polyphenyl polyisocyanate mixture using any of the known prior art phosgenation methods (see for example U.S. Pat. No. 4,465,639).

The properties of the polyamine product in respect of oligomer distribution and viscosity are determined on aliquot samples taken at various intervals during the continuous run. This data is set forth in Table I under Control samples 1 to 3. Sample #1 is taken as 0 sampling time with 2 and 3 being sampled 47 and 50 hours respectively into the continuous run. Also the polyisocyanate product obtained by phosgenation of the polyamine product is analyzed for various properties including, most notably, the Yellow Index color value which properties are set forth in Table II under Control samples 1 and 2 with Yellow Index values of 31.7 and 32, respectively.

A continuous process in accordance with the present invention is carried out by starting a continuous run as identically described above except as noted below and by recycling a minor proportion of the aniline free mixture obtained from the aniline stripping step back to the recirculation cooler loop of the intermediate reaction tank. The polyamine mixture recycled to the loop represents about 20 percent by weight of the initial aniline, aniline hydrochloride and formaldehyde charge. At the same time the volume ratio of aniline hydrochloride solution to formalin is increased to a ratio of 2.68 to reduce the viscosity of the resulting polyamine back to approximately the same level as obtained in the nonrecycle process. The addition of hydrochloric acid is increased due to the recycled amine so as to maintain the 0.25 meq. level set forth above. Also, the residence times in the intermediate reaction tank and final reactor are lowered to 17 minutes and 50 minutes, respectively.

Proton nuclear magnetic resonance analysis of a sample from the loop of the intermediate reaction tank analyzes out in percent by weight of aminal (formulae I and II above): aminobenzylamines (formulae III and IV): polymeric MDA as 3.3:45.5:51.2.

The caustic neutralizing and aniline stripping steps are carried out identically to those set forth above.

The polyamine mixture is continuously phosgenated using the identical procedure employed in phosgenating the above control polyamine mixture.

The properties of the polyamine product are determined similarly to the control samples of polyamine and are identified as Recycle Samples 1 to 4 set forth in Table I. Recycle Sample 1 is taken as 0 time with Recycle Samples 2, 3 and 4 being sampled 24, 48, and 74.5 hours, respectively, into the polyamine production. The polyisocyanate mixture produced from the polyamine of the present invention was sampled as Recycle Samples 1 to 4 set forth in Table II.

Notably, the Yellow Index values set forth in Table II for the Recycle Samples 1 to 4 are all considerably lower (average of 35% improvement) than those corresponding values for the Control Samples 1 and 2.

It should also be noted that the data set forth in Table I shows clearly that this improvement in color of the polyisocyanate is achieved with no real alteration in the properties of either the polyamine mixture or the final polyisocyanate.

TABLE I

| | Polyamine Products | | | | | | |
|---|---|---|---|---|---|---|---|
| | Control Samples* | | | Recycle Samples** | | | |
| | #1 | #2 | #3 | #1 | #2 | #3 | #4 |
| Oligomer Distribution % by wt.[1] | | | | | | | |
| MDA | 51.4 | 49.6 | 47.7 | 48.8 | 49.9 | 49.0 | 48.7 |
| Trimer | 23.5 | 23.6 | 23.8 | 22.8 | 22.7 | 22.6 | 22.5 |
| Tetramer | 11.8 | 12.2 | 12.7 | 11.9 | 11.8 | 11.8 | 11.8 |
| Pentamer | 6.1 | 6.5 | 7.0 | 6.5 | 6.6 | 6.5 | 6.6 |
| Hexamer | 3.2 | 3.7 | 4.0 | 3.9 | 3.9 | 3.9 | 4.0 |
| Heptamer | 4.0 | 4.4 | 4.8 | 6.1 | 5.1 | 6.2 | 6.4 |
| % p,p' MDA[2] | 92.8 | 92.7 | 92.7 | 91.5 | 92.8 | 91.8 | 91.6 |
| Viscosity (cstk) @ 70° C. | 260 | 350 | 438 | 388 | 359 | 376 | 418 |

*Sampling interval: #1 = 0; #2 = #1 + 47 hrs.; #3 = #1 + 50 hrs.
**Sampling interval: #1 = 0; #2 = #1 + 24 hrs.; #3 = #1 + 48 hrs.; #4 = #1 + 74.5 hrs.
[1]Measured by gel permeation chromatography.
[2]Measured by gas chromatography using flame ionization detector.

TABLE II

| | Polyisocyanate Products | | | | | |
|---|---|---|---|---|---|---|
| | Control Samples* | | Recycle Samples** | | | |
| | #1 | #2 | #1 | #2 | #3 | #4 |
| Isocyanate E.W. | 132.1 | 132.5 | 132.1 | 132.4 | 131.9 | 131.3 |
| % Hot HCl[1] | 0.04 | 0.04 | 0.04 | 0.04 | 0.04 | 0.04 |
| % Total hydrolyzable Cl[1] | 0.31 | 0.23 | 0.26 | 0.29 | 0.29 | 0.27 |
| Viscosity cps. @ 25° C. | 174 | 173 | 179 | 190 | 196 | 164 |
| Oligomer Distribution % by wt.[2] | | | | | | |
| MDI | 42.8 | 42.9 | 42.9 | 42.9 | 42.3 | 43.6 |
| Trimer | 19.1 | 19.6 | 19.0 | 19.2 | 19.2 | 19.4 |
| Tetramer | 10.1 | 10.3 | 10.1 | 10.3 | 10.4 | 10.4 |
| Pentamer | 6.3 | 6.4 | 6.6 | 6.6 | 6.7 | 6.5 |
| Hexamer | 21.7 | 20.8 | 21.4 | 21.0 | 21.4 | 20.1 |
| % p,p'-MDI | 92.1 | 92.2 | 91.1 | 90.8 | 90.7 | 90.6 |

TABLE II-continued

| | Polyisocyanate Products | | | | | |
|---|---|---|---|---|---|---|
| | Control Samples* | | Recycle Samples** | | | |
| | #1 | #2 | #1 | #2 | #3 | #4 |
| Yellow Index[3] | 31.7 | 32.0 | 19.1 | 22.9 | 20.4 | 21.4 |

*Sampling interval: #1 = 0; #2 = #1 + 24 hrs.
**Sampling interval: #1 = 0; #2 = #1 + 35 hrs.; #3 = #1 + 46 hrs.; #4 = #1 + 132 hrs.
[1]Test procedure described in U.S. Pat. No. 3,793,362 (col. 7, line 24 to col. 8, line 12).
[2]Measured by gel permeation chromatography.
[3]Yellow Index test performed by ASTM Method D1925-70.

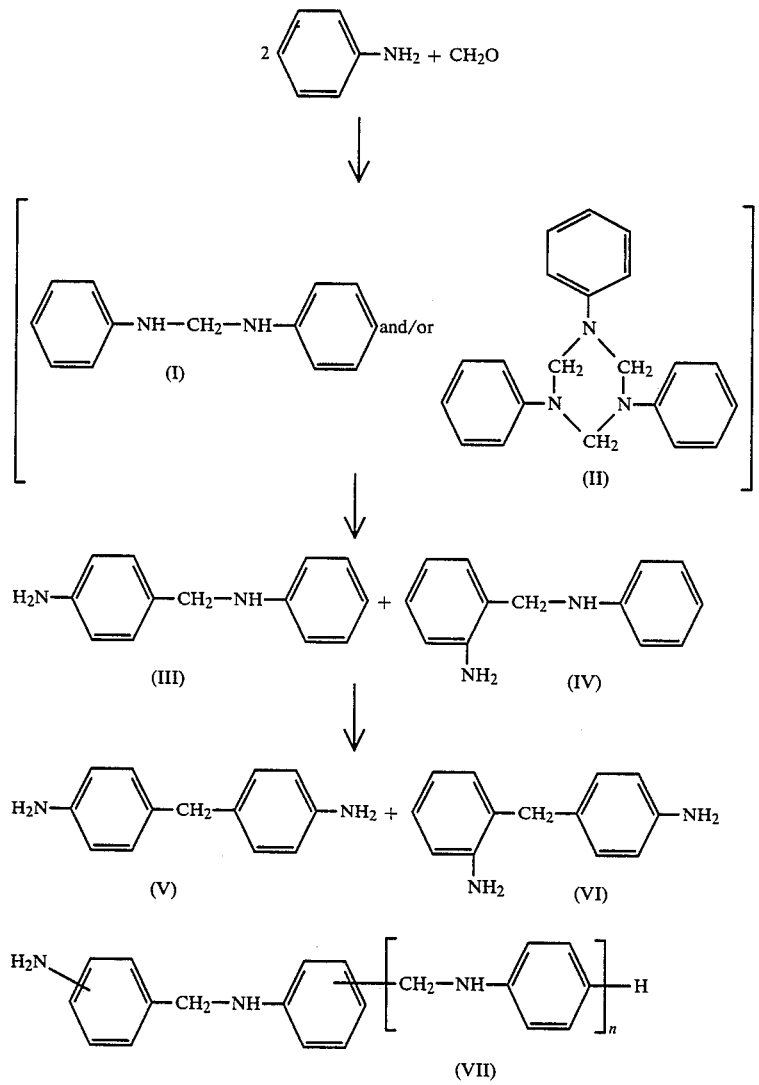

FORMULA CHART

We claim:

1. In a process for the preparation of a polyamine mixture comprising di(aminophenyl)methane and oligomeric polymethylene polyphenyl polyamines by the acid catalyzed reaction of aniline with formaldehyde to sequentially form a mixture comprising aminobenzylamines which latter subsequently rearrange with heat to form a reaction product comprising said polyamine mixture, the improvement which comprises adding an aniline free mixture of di(aminophenyl) methanes and oligomeric polymethylene polyphenyl polyamines to said sequentially formed aminobenzylamine mixture comprising at least 40 percent by weight of said aminobenzylamines prior to their said rearrangement to said polyamine mixture.

2. A process according to claim 1 wherein about 1.6 to about 8 moles of aniline per mole of formaldehyde are reacted in the presence of hydrochloric acid to sequentially form said aminobenzylamines.

3. A process according to claim 2 wherein said reaction is carried out at a temperature of from about 0° C. to about 55° C.

4. A process according to claim 3 wherein said rearrangement is carried out at a temperature of from about 60° C. to about 200° C.

5. A process according to claim 1 wherein said reaction product is neutralized followed by separation of an organic layer followed by distillation of aniline from said organic layer to provide said polyamine mixture essentially aniline free.

6. A process according to claim 5 wherein a major proportion of said aniline free polyamine mixture is recovered and a minor proportion is recycled as said aniline free mixture of di(aminophenyl)methane and oligomeric polymethylene polyphenyl polyamines to a mixture of aminobenzylamines produced in a subsequent reaction of aniline and formaldehyde to prepare said polyamine mixture.

7. A process according to claim 6 wherein the minor proportion of said aniline free polyamine mixture is from about 1 to about 40 percent by weight based on the combined initial weight of aniline, aniline salt and formaldehyde.

8. A continuous process for the preparation of a polyamine mixture comprising di(aminophenyl)methanes and oligomeric polymethylene polyphenyl polyamines which process comprises the steps of:
(a) intimately intermixing at a temperature of about 0° C. to about 55° C., rapidly flowing streams of aqueous aniline hydrochloride and aqueous formaldehyde in the proportions of about 1.6 to about 8 moles of aniline per mole of formaldehyde, at the entry port of a continuous tubular reactor to fom initially a mixture comprising aminobenzylamines;
(b) continuously passing said mixture from (a) through an intermediate cooling reaction zone wherein said aminobenzylamines can increase to at least about 40 percent by weight;
(c) continuously removing reaction mixture from said cooling zone at a rate corresponding to that at which reaction mixture is fed to said cooling zone;
(d) continuously passing said mixture from (c) through a rearrangement zone at a temperature of from about 60° C. to about 200° C. thereby forming said polyamine mixture;
(e) continuously removing said polyamine mixture from (d) at a rate corresponding to that at which the reaction mixture was fed into said rearrangement zone;
(f) continuously passing said mixture from (e) to a neutralizing zone causing said hydrochloric acid component to be neutralized followed by distilling aniline and water from said polyamine mixture to produce an essentially aniline free polyamine mixture comprising said di(aminophenyl)methane and said oligomeric polymethylene polyphenyl polyamines;
(g) continuously removing said polyamine mixture from step (f) at a rate to correspond with that at which the reaction mixture was fed into said neutralizing and distilling zones;
(h) passing a major portion of said polyamine mixture product to storage while recycling a minor proportion to a subsequent step (b) described above in such proportions that said recycle polyamine comprises from about 1 to about 40 percent by weight based on the combined initial weights of aniline, aniline hydrochloride and formaldehyde; and
(i) repeating steps (a) to (h) so as to continually pass said major proportion of polyamine mixture to storage while recycling the minor proportion back to step (b).

9. A process according to claim 8 wherein the aniline to formaldehyde ratio is increased by about 10 to about 50 percent in subsequent steps (a) after the initial one and provided the ratio still falls within the range set forth in claim 8.

10. A process according to claim 9 wherein the hydrochloric acid proportion employed in forming said aniline hydrochloride is increased so as to maintain a constant ratio of acid to amine equivalents.

* * * * *